(12) United States Patent
Naidu

(10) Patent No.: US 8,293,930 B1
(45) Date of Patent: Oct. 23, 2012

(54) ONE POT SYNTHESIS OF TAXANE DERIVATIVES AND THEIR CONVERSION TO PACLITAXEL AND DOCETAXEL

(75) Inventor: Ragina Naidu, Burnaby (CA)

(73) Assignee: Chatham Biotec, Limited, Riverview, New Brunswick (CA)

( * ) Notice: Subject to any disclaimer, the term of this patent is extended or adjusted under 35 U.S.C. 154(b) by 1286 days.

(21) Appl. No.: 11/630,510

(22) PCT Filed: Jun. 23, 2005

(86) PCT No.: PCT/US2005/022844
§ 371 (c)(1),
(2), (4) Date: Nov. 13, 2007

(87) PCT Pub. No.: WO2006/004708
PCT Pub. Date: Jan. 12, 2006

(51) Int. Cl.
*C07D 305/00* (2006.01)
(52) U.S. Cl. .......................... 549/510; 549/511
(58) Field of Classification Search ............... 549/511, 549/510, 214
See application file for complete search history.

(56) References Cited

U.S. PATENT DOCUMENTS

| | | | |
|---|---|---|---|
| 5,319,112 A | 6/1994 | Kingston et al. |
| 5,336,785 A | 8/1994 | Holton |
| 5,380,916 A | 1/1995 | Rao |
| 5,530,020 A | 6/1996 | Gunawardana et al. |
| 5,688,977 A | 11/1997 | Sisti et al. |
| 5,703,247 A | 12/1997 | Kingston et al. |
| 5,808,113 A | 9/1998 | Murray et al. |
| 6,136,989 A | 10/2000 | Foo et al. |
| 6,197,981 B1 | 3/2001 | Liu |
| 6,222,053 B1 | 4/2001 | Zamir et al. |
| 6,576,777 B2 | 6/2003 | Zamir et al. |
| 6,846,937 B2 | 1/2005 | Earhardt et al. |
| 7,202,370 B2 | 4/2007 | Naidu |
| 2001/0014746 A1 | 8/2001 | Holton |
| 2001/0037020 A1 | 11/2001 | Holton |
| 2001/0041803 A1 | 11/2001 | Kasitu et al. |
| 2008/0033189 A1 | 2/2008 | Naidu |
| 2008/0146824 A1 | 6/2008 | Naidu et al. |
| 2008/0262250 A1 | 10/2008 | Naidu |

FOREIGN PATENT DOCUMENTS

| | | |
|---|---|---|
| EP | 1403261 | 3/2004 |
| EP | 1786798 | 6/2008 |
| WO | 98/50378 | 11/1998 |
| WO | 99/54322 | 10/1999 |
| WO | WO 2004/033442 | 4/2004 |
| WO | WO 2004/033442 A2 | 4/2004 |

(Continued)

OTHER PUBLICATIONS

Office action from the U.S. Patent and Trademark Office in U.S. Appl. No. 11/587,407, dated Nov. 27, 2009.

(Continued)

*Primary Examiner* — Noble Jarrell
*Assistant Examiner* — Raymond Covington
(74) *Attorney, Agent, or Firm* — Klarquist Sparkman, LLP

(57) ABSTRACT

A process is provided for the semi-synthesis of taxane intermediates useful in the preparation of paclitaxel and docetaxel, in particular, the semi-synthesis of protected taxane intermediate in a one pot reaction of protecting the C-7 and C-10 positions and attaching a side chain at the C-13 position and subsequently deprotecting the group to form paclitaxel or docetaxel, and taxane intermediates.

34 Claims, 3 Drawing Sheets

FOREIGN PATENT DOCUMENTS

| WO | 2005/082875 | 9/2005 |
|---|---|---|
| WO | 2005/105767 | 11/2005 |
| WO | 2005/118563 | 12/2005 |
| WO | 2006/004898 | 1/2006 |

OTHER PUBLICATIONS

Office action from the U.S. Patent and Trademark Office in U.S. Appl. No. 11/628,428, dated Feb. 3, 2010.

Nicolaou et al., "Chemistry and Biology of Taxol," *Angew. Chem. Int. Ed. Engl.* 33:15-44, 1994.

Klein, L., "Synthesis of 9-Dihydrotaxol: A Novel Bioactive Taxane," *Tetrahedron Letters*, vol. 34, No. 13, pp. 2047-2050 (Mar. 26, 1993).

Notice of Allowance from the U.S. Patent and Trademark Office in U.S. Appl. No. 11/587,407, dated Jul. 22, 2010.

Office Action from European Patent Office in European Patent Application No. 05760288.0, dated Jul. 23, 2009.

Office action from the U.S. Patent and Trademark Office in U.S. Appl. No. 11/631,466, dated Mar. 12, 2010.

Beckvermit et al., "An Improved Method for Separating Paclitaxel and Cephalomannine Using Ozone and Girard Reagents," J. Org. Chem., vol. 61, No. 25, pp. 9038-9040 (1996).

Chen et al., "Synthesis and Biological Evaluation of Novel C-4 Aziridine-Bearing Paclitaxel (Taxol) Analogs," CAPLUS 123:112445, Abstract Only, *Journal of Medicinal Chemistry*, vol. 38, No. 12, pp. 2263-2267 (1995).

Commerçon et al., "Improved Protection and Esterification of a Precursor of the Taxotere® and Taxol Side Chains," *Tetrahedron Letters*, vol. 33, No. 36, pp. 5185-5188 (1992).

Final Office action from the U.S. Patent and Trademark Office in U.S. Appl. No. 11/587,407, dated Apr. 16, 2009.

Final Office action from the U.S. Patent and Trademark Office in U.S. Appl. No. 11/631,466, dated Jul. 20, 2009.

Gennari et al., "Computer-Assisted Design and Synthetic Applications of Chiral Enol Borinates: Novel, Highly Enantioselective Aldol Reagents," *J. Braz. Chem. Soc.*, vol. 9, No. 4, pp. 319-326 (1998).

Gennari et al., "Rationally designed chiral enol borinates: Powerful reagents for the stereoselective synthesis of natural products," *Pure & Appl. Chem.*, vol. 69, No. 3, pp. 507-512 (1997).

International Search Report for PCT/US2005/014080 (mailed Aug. 3, 2005).

International Search Report for PCT/US2005/005953 (mailed Sep. 14, 2005).

International Search Report for PCT/US2005/019697 (mailed Sep. 28, 2005).

International Search Report for PCT/US2005/023224 (mailed Jan. 25, 2006).

Kanazawa et al., "Highly Stereocontrolled and Efficient Preparation of the Protected, Esterification-Ready Docetaxel (Taxotere) Side Chain," *Journal of Organic Chemistry*, vol. 59, pp. 1238-1240 (1994).

Office action from the U.S. Patent and Trademark Office in U.S. Appl. No. 10/590,647, dated Sep. 19, 2008.

Office action from the U.S. Patent and Trademark Office in U.S. Appl. No. 11/587,407, dated Sep. 25, 2008.

Office action from the U.S. Patent and Trademark Office in U.S. Appl. No. 11/628,428, dated Sep. 4, 2009.

Office action from the U.S. Patent and Trademark Office in U.S. Appl. No. 11/631,466, dated Jul. 24, 2008.

Office action from the U.S. Patent and Trademark Office in U.S. Appl. No. 11/631,466, dated Jan. 26, 2009.

Pines et al., "The Stereochemistry of 2,3-Diphenyl-1-methylpropylamine," *Journal of Medical Chemistry*, vol. 10, No. 4, pp. 725-728 (1967).

Rimoldi et al., "An Improved Method for the Separation of Paclitaxel and Cephalomannine," *Journal of Natural Products*, vol. 59, No. 2, pp. 167-168 (1996).

International Preliminary Report on Patentability for PCT/US2005/022844 (mailed Dec. 28, 2006).

International Search Report for PCT/US2005/022844 (mailed Oct. 20, 2005).

Notice of Allowance from the U.S. Patent and Trademark Office in U.S. Appl. No. 11/628,428, dated Oct. 14, 2010.

Notice of Allowance from the U.S. Patent and Trademark Office in U.S. Appl. No. 11/631,466, dated Nov. 19, 2010.

International Search Report for PCT/US2005/022844.

ONE POT SYNTHESIS OF TAXANE DERIVATIVES AND THEIR CONVERSION TO PACLITAXEL AND DOCETAXEL

CROSS REFERENCE TO RELATED APPLICATIONS

This is the U.S. National Stage of International Application No. PCT/US2005/022844, filed Jun. 23, 2005, which was published in English under PCT Article 21(2), which claims the benefit of U.S. application Ser. No. 10/877,789, filed Jun. 25, 2004.

BACKGROUND OF THE INVENTION

1. Field of the Invention

The present invention relates to the semi-synthesis of taxane derivatives useful in the preparation of paclitaxel and docetaxel, in particular, the semi-synthesis of protected taxane derivatives in a one pot reaction.

2. Description of the Related Art

The taxane family of terpenes has received much attention in the scientific and medical community because members of this family have demonstrated broad spectrum anti-leukemic and tumor-inhibitory activity. A well-known member of this family is paclitaxel (1, Taxol).

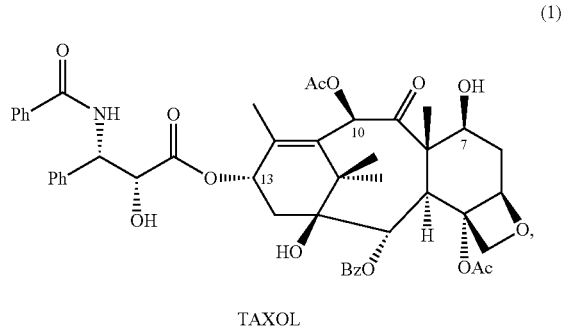

TAXOL

Paclitaxel was first isolated from the bark of the pacific yew tree (*Taxus brevifolia*) in 1971, and has proved to be a potent natural anticancer agent. For example, paclitaxel has been found to have activity against different forms of leukemia and against solid tumors in the breast, ovary, brain, and lung in humans.

This activity has stimulated an intense research effort over recent years, including the search for other taxanes having similar or improved properties, and the development of synthetic pathways for making taxanes such as paclitaxel. One result from this research effort was the discovery of a synthetic analog of paclitaxel, docetaxel (2, more commonly known as taxotere). As disclosed in U.S. Pat. No. 4,814,470, taxotere has been found to have very good anti-tumor activity and better bio-availability than paclitaxel. Taxotere is similar in structure to paclitaxel, having t-butoxycarbonyl instead of benzoyl on the amino group at the 3' position, and a hydroxy group instead of the acetoxy group at the C-10 position.

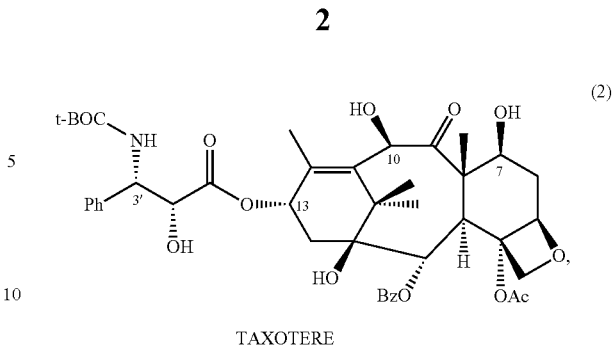

TAXOTERE

Taxanes are structurally complicated molecules, and the development of commercially viable synthetic methods to make taxanes has been a challenge. A number of semi-synthetic pathways have been developed, which typically begin with the isolation and purification of a naturally occurring material followed by its conversion to a taxane of interest. For example, paclitaxel and taxotere may be prepared semi-synthetically from 10-deacetylbaccatin III or baccatin III as set forth in U.S. Pat. No. 4,924,011 to Denis et al. and U.S. Pat. No. 4,924,012 to Colin et al. or by the reaction of a beta-lactam and a suitably protected 10-deacetylbaccatin III or baccatin III derivative as set forth in U.S. Pat. No. 5,175,315 to Holton et al. or U.S. patent application Ser. No. 10/683,865, which application is assigned to the assignee of the present invention. 10-deacetylbaccatin III (10-DAB, 3) and baccatin III (BACC III, 4) can be separated from mixtures extracted from natural sources such as the needles, stems, bark or heartwood of numerous *Taxus* species and have the following structures:

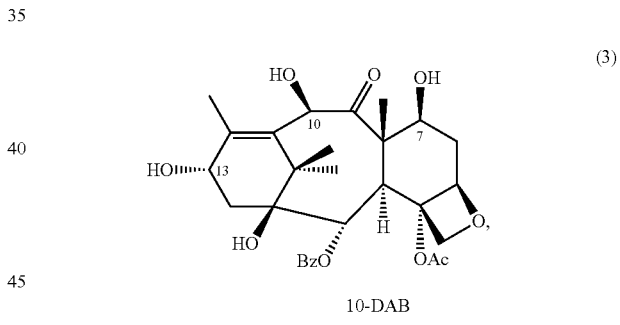

10-DAB

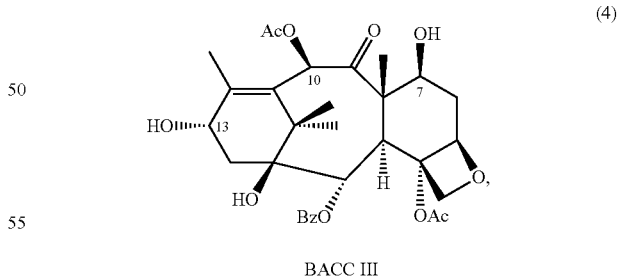

BACC III

Although much of the research towards the semi-synthesis of paclitaxel and taxotere has involved 10-deacetylbaccatin III as the starting material, other taxanes from the *Taxus* species, such as 9-dihydro-13-acetylbaccatin III (9-DHB, 5), present in the Canadian yew (*Taxus Canadensis*), cephalomannine (6), 10-deacetyl taxol (10-DAT, 7), 7-xylosyl taxol (8), 10-deacetyl-7-xylosyl taxol (9) and a number of 7-epitaxanes have been collected and identified.

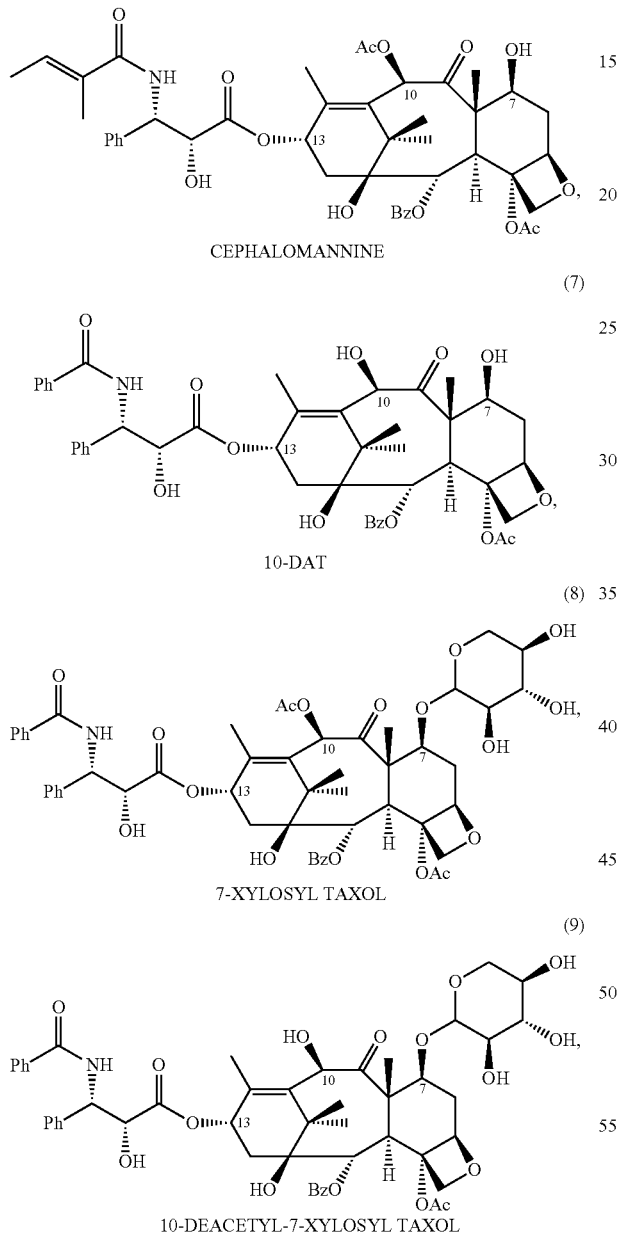

9-DHB (5)

CEPHALOMANNINE (6)

10-DAT (7)

7-XYLOSYL TAXOL (8)

10-DEACETYL-7-XYLOSYL TAXOL (9)

In addition, U.S. Pat. Nos. 5,202,448 and 5,256,801 to Carver et al., U.S. Pat. No. 5,449,790 to Zheng et al. and U.S. Pat. No. 6,281,368 to McChesney et al. disclose processes for converting certain taxanes (namely, paclitaxel, cephalomannine, 10-deacetyl taxol and certain 10-deacetyl taxol derivatives) present in partially purified taxane mixtures into 10-deacetylbaccatin III and baccatin III, which may subsequently be utilized in the foregoing semi-synthetic pathways.

Although there have been many advances in the field, there remains a need for new and improved processes for the preparation of taxane derivatives and their conversion to paclitaxel and docetaxel, and also for the preparation of such taxane intermediates from crude and partially purified mixtures comprising a plurality of taxanes. The present invention addresses these needs and provides further related advantages.

BRIEF SUMMARY OF THE INVENTION

In brief, the present invention relates to the semi-synthesis of taxane intermediates useful in the preparation of paclitaxel and docetaxel, in particular, the semi-synthesis of protected taxane intermediates in a one pot reaction. As set forth below, In one embodiment, the present invention provides a process for protecting a taxane of Formula (I):

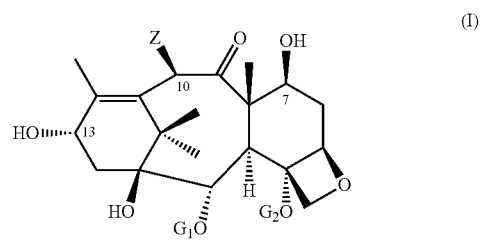

(I)

wherein, Z is —OH or a protected —OH, $G_1$ and $G_2$ are the same or different and independently a hydroxy protecting group, the process comprising: protecting the free hydroxy groups at the C-7 position and/or the C-10 position of the taxane, and attaching a side chain to the free hydroxy group at the C-13 position of the taxane to provide a C-13 protected taxane intermediate, wherein the steps of protecting and attaching comprises, in a one-pot reaction, combining the taxane with a base, a suitable hydroxy protecting agent and a precursor to the side chain, and wherein the precursor to the side chain is a beta-lactam, oxazolidine or oxazoline.

In a further embodiment, the present invention provides a process for protecting a taxane of Formula (I), which is part of a mixture of taxanes comprising, in addition to the taxane of Formula (I), paclitaxel, 9-dihydro-13-acetylbaccatin III, cephalomannine, 10-deacetyl taxol, 7-xylosyl taxol and 10-deacetyl-7-xylosyl taxol.

In another embodiment, the present invention provides a process for preparing paclitaxel or docetaxel, comprising: protecting the hydroxy group at the C-7 and/or C-10 position of a compound of formula (V):

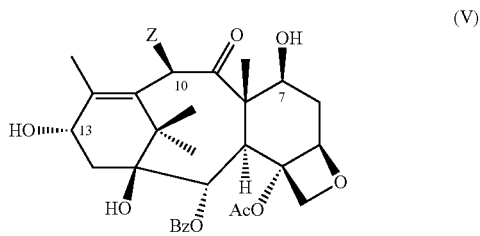

(V)

wherein, Z is —OH or protected —OH; attaching a side chain to the free hydroxyl group at C-13 position to provide a C-13 protected taxane intermediate; and converting the C-13 protected taxane intermediate to paclitaxel or docetaxel, wherein the steps of protecting and attaching comprise, combining in a one pot reaction, the compound of Formula (V) with a base, a suitable hydroxy protecting agent and a precursor to the side chain, and wherein the precursor to the side chain is a beta-lactam, oxazolidine or oxazoline.

In yet another embodiment, the present invention provides a process for preparing paclitaxel or docetaxel from an initial mixture of taxanes comprising 10-deacetylbaccatin III and at least one additional taxane selected from paclitaxel, 9-dihydro-13-acetylbaccatin III, baccatin III, cephalomannine, 10-deacetyl taxol, 7-xylosyl taxol and 10-deacetyl-7-xylosyl taxol, the process comprising: protecting the hydroxy group at the C-7 position of each taxane in the initial mixture having a hydroxy group at the C-7 position to yield a first intermediate mixture of C-7 protected taxanes; attaching a side chain to the C-13 position of each taxane having a free hydroxy group at the C-13 position in the first intermediate mixture to provide a mixture of C-13 protected taxane intermediates; and converting the C-13 protected taxane intermediates to paclitaxel or docetaxel, wherein, the steps of protecting the C-7 hydroxy groups and attaching a side chain to the free hydroxyl at the C-13 position comprises: combining, in a one pot reaction, the initial mixture with a base, a suitable hydroxy protecting agent and a precursor to the side chain, and wherein the precursor to the side chain is a beta-lactam, oxazolidine or oxazoline.

These and other aspects of the invention will be apparent upon reference to the attached figures and following detailed description.

DETAILED DESCRIPTION OF THE INVENTION

Figure 1:
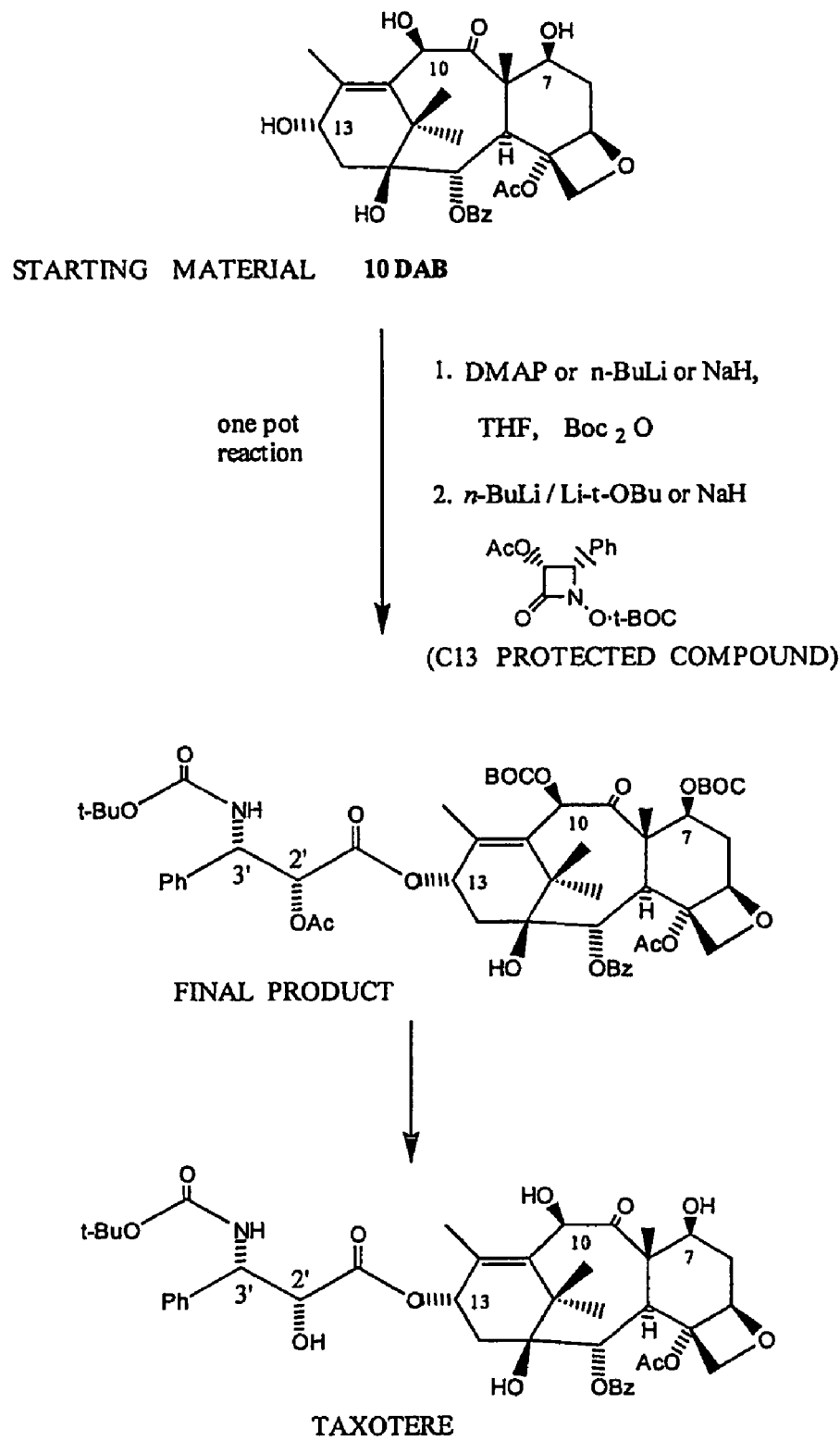
FIG. 1 illustrates a chemical route for the preparation of a C-13 beta-lactam protected taxane intermediate, and the conversion of such intermediate to docetaxel according to the present invention.

As mentioned above, the present invention relates to the semi-synthesis of taxane intermediates useful in the preparation of paclitaxel and docetaxel, in particular, the semi-synthesis of protected taxane intermediates in a one pot reaction.

I. Definitions

As used herein, the following terms have the following meanings.

"Silica matrix" is a solid media containing a silicate which is used as an adsorbent or column material in chromatographic separations, including (but not limited to) ordinary silica, Florisil, porous silica gels or any physical formulation of a silicate for use in chromatographic procedures.

"Taxane-containing material" refers to selected parts of a plant, plant tissues, cell cultures, microorganisms or extracts with extractable taxanes, including paclitaxel, 10-deacetyl-baccatin III (10-DAB), baccatin III (BACC III), 9-dihydro-13-acetylbaccatin III (9-DHB), cephalomannine, 10-deacetyl taxol (10-DAT), 7-xylosyl taxol and 10-deacetyl-7-xylosyl taxol.

"Crude taxane extract" refers to a composition obtained from a taxane-containing material by treating the taxane-containing material with at least one solvent.

"Partially purified taxane extract" refers to a paclitaxel enriched composition obtained from the chromatographic separation and/or recrystallization of a crude or partially purified taxane extract.

"Waste stream fractions" refers to fractions collected following the chromatographic separation and collection of paclitaxel enriched fractions from a crude or partially purified taxane extract by, for example, the process of U.S. Pat. No. 6,136,989.

"Waste mother liquors" refers to mother liquors collected following the recrystallization of a crude or partially purified taxane extract by, for example, the process of U.S. Pat. No. 6,136,989.

"Hydroxy-protecting group" refers to any derivative of a hydroxy group known in the art which can be used to mask the hydroxy group during a chemical transformation and later removed under conditions resulting in the hydroxy group being recovered without other undesired effects on the remainder of the molecule. Many esters, acetals, ketals and silyl ethers are suitable protecting groups. Examples of hydroxy-protecting groups include, without limitation, formyl, acetyl (Ac), benzyl (PhCH$_2$), 1-ethoxyethyl (EE), methoxymethyl (MOM), (methoxyethoxy)methyl (MEM), (p-methoxyphenyl)methoxymethyl (MPM), tert-butyldimethylsilyl (TBS), tert-butyldiphenylsilyl (TBPS), tert-butoxycarbonyl (tBoc, t-Boc, tBOC, t-BOC), tetrahydropyranyl (THP), triphenylmethyl (Trityl, Tr), 2-methoxy-2-methylpropyl, benzyloxycarbonyl (Cbz), dichloroacetyl, trichloroacetyl (OCCCl$_3$), 2,2,2-trichloroethoxycarbonyl (Troc), benzyloxymethyl (BOM), tert-butyl (t-Bu), triethylsilyl (TES), trimethylsilyl (TMS), triisopropylsilyl (TIPS), propionyl, isopropionyl, pivalyl, dimethylisopropylsilyl, diethylisopropylsilyl, methyldiphenylsilyl, dimethylphenylsilyl, tert-butyldiphenylsilyl, tribenzylsilyl, triphenylsilyl, trichloroethoxycarbonyl, benzyl, para-nitrobenzyl, para-methoxybenzyl, benzoyl, methoxyethyl, para-methoxyphenyl, tetrahydrofuranyl, alkylsulfonyl and arylsulfonyl. The related term "protected hydroxy group" or "protected —OH" refers to a hydroxy group that is bonded to a hydroxy-protecting group. General examples of protected hydroxy groups include, without limitation, —O-alkyl, —O-acyl, acetal, and —O-ethoxyethyl, where some specific protected hydroxy groups include, formyloxy, acetoxy, propionyloxy, chloroacetoxy, bromoacetoxy, dichloroacetoxy, trichloroacetoxy, trifluoroacetoxy, methoxyacetoxy, phenoxyacetoxy, benzoyloxy, benzoylformoxy, p-nitro benzoyloxy, ethoxycarbonyloxy, methoxycarbonyloxy, propoxycarbonyloxy, 2,2,2-trichloroethoxycarbonyloxy, benzyloxycarbonyloxy, tert-butoxycarbonyloxy, 1-cyclopropylethoxycarbonyloxy, phthaloyloxy, butyryloxy, isobutyryloxy, valeryloxy, isovaleryloxy, oxalyoxy, succinyloxy and pivaloyloxy, phenylacetoxy, phenylpropionyloxy, mesyloxy, chlorobenzoyloxy, para-nitrobenzoyloxy, para-tert-butyl benzoyloxy, capryloyloxy, acryloyloxy, methylcarbamoyloxy, phenylcarbamoyloxy, naphthylcarbamoyloxy, and the like. The related term "hydroxy protecting agent" refers to a reagent that introduces a hydroxy protecting group to a free hydroxy functionality. Typically, a hydroxy protecting agent comprises a hydroxy protecting group as those listed above and a leaving group, such as a halide or a triflate. When the hydroxy protecting group is an alkyl, the hydroxy protecting agent is referred herein as an alkylating agent. Similarly, when the hydroxy protecting group is an acyl or silyl, the hydroxy protecting agent can be referred herein as an acylating agent or silylating agent, respectively. More exemplary hydroxy-protecting groups and hydroxy protecting agents are described in, e.g., C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3.

"Thiol-protecting group" refers to any derivative of a thiol group known in the art which can be used to mask the thiol group during a chemical transformation and later removed under conditions resulting in the thiol group being recovered without other undesired effects on the remainder of the molecule. Examples of thiol-protecting groups include, without limitation, triphenylmethyl (trityl, Trt), acetamidomethyl (Acm), benzamidomethyl, 1-ethoxyethyl, benzoyl, and the like. The related term "protected thiol group" refers to a thiol group that is bonded to a thiol-protecting group. General examples of protected thiol groups include, without limitation, —S-alkyl (alkylthio, e.g., $C_1$-$C_{10}$alkylthio), —S-acyl (acylthio), thioacetal, —S-aralkyl (aralkylthio, e.g., aryl($C_1$-$C_4$)alkylthio), where some specific protected thiols groups include methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio and cyclohexylthio, benzylthio, phenethylthio, propionylthio, n-butyrylthio and iso-butyrylthio. Thiol-protecting groups and protected thiol groups are described in, e.g., C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3.

The following Table shows the chemical structures of some protecting groups, as well as the nomenclatures used to identify these chemical structures.

TABLE 1

| Acetyl (Ac) | $H_3C-C(=O)-$ |
| Acetoxy (—OAc) | $H_3C-C(=O)-O-$ |
| Dichloroacetyl | $H-C(Cl)_2-C(=O)-$ |
| Dichloroacetoxy | $H-C(Cl)_2-C(=O)-O-$ |
| Triethylsilyl (TES) | $H_3CH_2C-Si(CH_2CH_3)_2-$ |
| Triethylsiloxy (—OTES) | $H_3CH_2C-Si(CH_2CH_3)_2-O-$ |
| Benzoyl | $Ph-C(=O)-$ |
| Benzoyloxy | $Ph-C(=O)-O-$ |
| t-Butyloxycarbonyl (tBOC) | $(H_3C)_3C-O-C(=O)-$ |
| t-Butoxycarbonyloxy (—O-tBOC) | $(H_3C)_3C-O-C(=O)-O-$ |
| para-Methoxyphenyl (PMP) | $H_3C-O-C_6H_4-$ |

"Alkyl" refers to an optionally substituted hydrocarbon structure, containing no saturation, wherein the carbons are arranged in a linear, branched or cyclic manner, including combinations thereof. Lower alkyl refers to alkyl groups of 1 to 5 carbon atoms. Examples of lower alkyl groups include methyl, ethyl, propyl, isopropyl, butyl, s- and t-butyl and the like. "Cycloalkyl" is a subset of alkyl and includes mono or bi-cyclic hydrocarbon groups of from 3 to 13 carbon atoms. Examples of cycloalkyl groups include cyclopropyl, cyclobutyl, cyclopentyl, norbornyl, adamantyl and the like. When an alkyl residue having a specific number of carbons is named, all geometric isomers having that number of carbons are intended to be encompassed; thus, for example, "butyl" is meant to include n-butyl, sec-butyl, isobutyl and t-butyl; propyl includes n-propyl and isopropyl.

"Alkenyl" refers to an optionally substituted alkyl group having at least one site of unsaturation, i.e., at least one double bond.

"Alkynyl" refers to an optionally substituted alkyl group having at least one triple bond between two adjacent carbon atoms.

"Alkoxy" refers to a radical of the formula —O-alkyl. Examples include methoxy, ethoxy, propoxy, isopropoxy, cyclopropyloxy, cyclohexyloxy and the like. Lower-alkoxy refers to groups containing one to five carbons.

"Alkoxycarbonyl" refers to a radical of the formula —C(O)-alkoxy, wherein alkoxy is as defined herein.

"Aryl" refers to optionally substituted phenyl or naphthyl. Exemplary substituents for aryl include one or more of halogen, hydroxy, alkoxy, aryloxy, heteroaryloxy, amino, alkylamino, dialkylamino, mercapto, alkylthio, arylthio, heteroarylthio, cyano, carboxyl, alkoxycarbonyl where the alkoxy portion contains 1 to 15 carbons, aryloxycarbonyl where the aryloxy portion contains 6 to 20 carbon, or heteroarylcarbonyl where the heteroaryl portion contains 3 to 15 carbon atoms.

"Aryloxy" refers to a radical of the formula —O-aryl, wherein aryl is defined as above. Representative aryloxy includes phenoxy.

"Aryloxycarbonyl" refers to a radical of the formula —C(O)-aryloxy, wherein aryloxy is as defined herein.

"Heteroaryl" refers to an optionally substituted 5- or 6-membered heteroaromatic ring containing 1-3 heteroatoms selected from O, N or S; a bicyclic 9- or 10-membered heteroaromatic ring system containing 1-3 heteroatoms selected from O, N or S; or a tricyclic 13- or 14-membered heteroaromatic ring system containing 1-3 heteroatoms selected from O, N or S. Exemplary aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

"Heterocycle" means a 5- to 7-membered monocyclic, or 7- to 10-membered bicyclic, heterocyclic ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be optionally substituted with 1-5 substituents. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Acyl" refers to a radical of the formula —C(=O)—R, wherein R is alkyl, alkenyl, alkynyl, aryl, alkoxy, aryloxy, heterocycle or heteroaryl, where alkyl, alkenyl, alkynyl, aryl, alkoxy, aryloxy, heterocycle and heteroaryl are as defined herein. Representative acyl groups include acetyl, benzoyl, propionyl, isobutyryl, t-butoxycarbonyl, and the like. Loweracyl refers to groups containing one to five carbons.

"Leaving group" refers to a chemical moiety that may be displaced during a substitution or elimination reaction. Exemplary leaving groups include halogen (e.g., bromide and chloride), triflate and tosyl.

"Halogen" refers to fluoro, chloro, bromo or iodo.

"Oxo" refers to =O.

"Hydrocarbonyl" refers to alkyl, alkenyl, alkynyl or aryl.

The term "substituted" as used herein means any of the above groups (e.g., alkyl, alkoxy, acyl, aryl, heteroaryl and heterocycle) wherein at least one hydrogen atom is replaced with a substituent. In the case of an oxo substituent ("=O") two hydrogen atoms are replaced. Substituents include halogen, hydroxy, oxo, alkyl, aryl, alkoxy, aryloxy, acyl, mercapto, cyano, alkylthio, arylthio, heteroarylthio, heteroaryl, heterocycle, —$NR_aR_b$, —$NR_aC(=O)R_b$, —$NR_cC(=O)NR_aR_b$, —$NR_aC(=O)OR_b$, —$NR_aSO_2R_b$, —$C(=O)NR_aR_b$, —$OC(=O)R_a$, —$OC(=O)OR_a$, —$OC(=O)NR_aR_b$, —$NR_aSO_2R_b$ or a radical of the formula —Y—Z—$R_a$ where Y is alkanediyl, substituted alkanediyl or a direct bond, alkanediyl refers to a divalent alkyl with two hydrogen atoms taken from the same or different carbon atoms, Z is —O—, —S—, —S(=O)—, —$S(=O)_2$—, —$N(R_b)$—, —C(=O)—, —C(=O)O—, —OC(=O)—, —$N(R_b)C(=O)$—, —$C(=O)N(R_b)$— or a direct bond, wherein $R_a$, $R_b$ and $R_c$ are the same or different and independently hydrogen, amino, alkyl, substituted alkyl (including halogenated alkyl), aryl, substituted aryl, heteroaryl, substituted heteroaryl, heterocycle or substituted heterocycle or wherein $R_a$ and $R_b$ taken together with the nitrogen atom to which they are attached form a heterocycle or substituted heterocycle.

The term "one pot reaction", also referred to herein as a "one pot synthesis" refers to a multi-step chemical reaction carried out in a reaction vessel. Typically, a reaction intermediate is generated in an initial step of reaction, the intermediate is then reacted in situ with other component(s) present in or introduced to the same vessel. The reaction intermediate generated is not isolated but serves directly as a reactant in a next step of reaction. For example, in one embodiment of the instant invention, a free hydroxy group of a taxane is protected, the protected intermediate is not isolated and is used directly in a next step wherein a side chain is attached to a free hydroxy group of the taxane intermediate.

II. Process for Preparing C-13 Protected Taxane Intermediates

The present invention relates to a semi-synthesis process of taxane intermediates useful in the preparation of paclitaxel and docetaxel, in particular, the semi-synthesis of protected taxane intermediates. Specifically, one embodiment of the present invention provides a process comprising novel combined steps of protecting the C7 and/or C10 positions of a taxane of Formula (I) and attaching a side chain to the free hydroxy group at C13 position in a one-pot reaction to provide a C13 protected taxane intermediate (III). The process comprises combining, in one reaction vessel, a taxane of Formula (I) with a base, a hydroxy protecting agent and a precursor to the side chain, for example, a compound of Formula (II). A general reaction scheme is shown below:

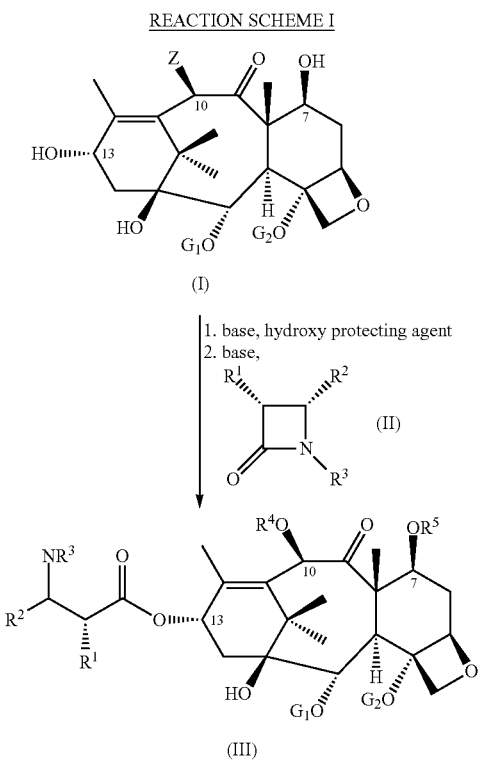

wherein,

R₁ is a hydroxy group, protected hydroxy group, thiol group or protected thiol group;

R₂ is alkyl, alkenyl, alkynyl or aryl;

R₃ is hydrogen, $C_1$-$C_6$ alkyl, aryl or acyl;

Z is —$OR^4$ or OH;

$R^4$ and $R^5$ are the same or different and independently a hydroxy protecting group; and $G_1$ and $G_2$ are the same or different and independently a hydroxy protecting group.

In one embodiment, wherein Z is —OH in Formula (I), the protection step comprises protecting the hydroxy groups at both C-7 and C-10 position, as a result, $R^4$ and $R^5$ of Formula (III) are the same hydroxy protecting group.

In a further embodiment, wherein Z is already protected, (i.e., Z is —$OR^4$), the protection step comprises protecting the hydroxy group at C-7 position only, as a result, $R^4$ and $R^5$ of Formula (III) can be the same or different hydroxy protecting groups.

In yet another embodiment, the precursor to the side chain can be an oxazolidine or oxazoline.

The foregoing protection and attachment steps are described below.

General Method of Protection

The hydroxy groups at the C-7 and/or C-10 positions of a taxane of Formula (I) can be selectively protected using any of a variety of hydroxy protecting agents, such as acetal, ketal, silyl, and removable acyl protecting groups, in the presence of a base, wherein Formula (I) is:

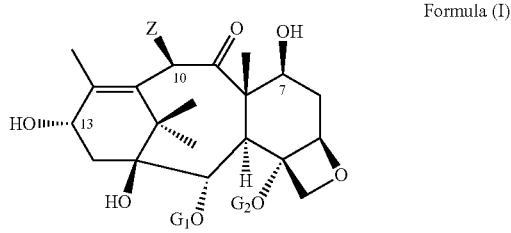

Formula (I)

wherein,

Z is —$OR^4$ or OH, and $R^4$, $G_1$ and $G_2$ are the same or different and independently a hydroxy protecting group.

In particular, the C-7 and/or C-10 hydroxy group may be silylated using any of a variety of common silylating agents including, but not limited to, tri(hydrocarbonyl)silyl halides and tri(hydrocarbonyl)silyl triflates. The hydrocarbonyl moieties of these compounds may be optionally substituted and preferably are substituted or unsubstituted alkyl or aryl. More specifically, the C-7 and/or C-10 hydroxy group can be selectively silylated, for example, using silylating agents such as tribenzylsilyl chloride, trimethylsilyl chloride, triethylsilyl chloride, dimethylisopropylsilyl chloride, dimethylphenylsilyl chloride and the like.

Alternatively, selective acylation of the C-7 and/or C-10 hydroxy group can be achieved using any of a variety of common acylating agents, but not limited to substituted and unsubstituted carboxylic acid derivatives, e.g., carboxylic acid halides, anhydrides, dicarbonates, isocyanates and haloformates. More specifically, the C-7 and/or C-10 hydroxy group can be selectively acylated, for example, with di-tert-butyl dicarbonate ($Boc_2O$), dibenzyl dicarbonate, diallyl dicarbonate, 2,2,2-trichloroethyl chloroformate, benzyl chloroformate, dichloroacetyl chloride, acetyl chloride or another common acylating agent.

Suitable base for the protecting step includes, for example, DMAP, pyridine, TEA, LiOH, Li-t-OBu, n-BuLi, LiH, LiHMDS, KHMDS, K-t-OBu, NaH, NaHMDS and a mixture of any two or more of the foregoing, such as a mixture of n-BuLi/Li-t-Obu.

Exemplary reaction conditions are as follows: a taxane of Formula (I), or a mixture of taxanes, is dissolved in an organic solvent, such as anhydrous DCM (dichloromethane) or THF (tetrahydrofuran) or DMF (dimethyl formamide) or DMSO (dimethyl sulfoxide) or acetonitrile under an argon atmosphere at low temperature. To this solution is added DMAP (dimethylaminopyridine) or any of the lithium, sodium or potassium base, such as Li-t-OBu, K-t-OBu, n-BuLi, a mixture of n-BuLi/K-t-OBu or LiOH, followed by a hydroxy protecting agent, such as an acylating agent (e.g., di-tert-butyl dicarbonate), a silylating agent (e.g., triethyl silyl chloride) or any other hydroxy protecting agent containing a hydroxy-protecting group. The mixture is left at low to room temperature until complete consumption of the starting material, as visualized by TLC to afford a C-7 and/or C-10 protected taxane or a mixture of C-7 and/or C-10 protected taxanes. "Low temperature" as used herein refers to temperature between –78 to room temperature.

Following protection of the hydroxy groups at the C-7 and/or C-10 position of a taxane using the foregoing process, the attachment of the side chain may be performed in the same vessel without isolating the product of the protection step according to the following method.

General Method of Attachment An ester linkage at the C-13 position of the above taxane may be formed in the same combined step by adding to the C-7 and C-10 protected taxane, a base and a precursor to the side chain. Representative base includes DMAP, TEA, LiOH, Li-t-OBu, n-BuLi, LiH, LiHMDS, KHMDS, K-t-OBu, NaH, NaHMDS or a mixture of any two or more of the foregoing. In addition, the combined step may further comprise combining the taxane with a metal alkoxide, wherein the metal is selected from the group consisting of Group I, II and III metals and transition metals. Representative precursors to the side chains are described in more detail below, and include beta-lactams of Formula (II):

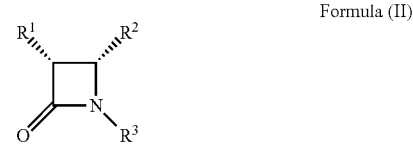

Formula (II)

wherein,

R₁ is a hydroxy group, protected hydroxy group, thiol group or protected thiol group;

R₂ is alkyl, alkenyl, alkynyl or aryl; and

R₃ is hydrogen, $C_1$-$C_6$ alkyl, aryl or acyl.

An exemplary reaction condition for the C-13 attachment includes, dissolving a taxane resulting from the preceding protection step and having a free hydroxy group at the C-13 position, or a mixture of taxanes, in an organic solvent under an argon temperature at low temperature, for example, –78° C. to room temperature. To this solution is added a base, such as DMAP, TEA, LiOH, Li-t-OBu, n-BuLi, LiH, LiHMDS, KHMDS, K-t-OBu, NaH, NaHMDS or a mixture of any two or more of the foregoing, followed by addition of a solution of beta-lactam. The mixture is left to react at low to room temperature until complete consumption of the starting material, as visualized by TLC. A solution of an acid, such as AcOH, in an organic solvent is added to the mixture, and the mixture is partitioned between saturated aqueous sodium hydrogen carbonate and mixtures of DCM and ethyl acetate. The combined organic extracts are dried and evaporated to give the crude C-13 beta-lactam protected taxane intermediate, which can be further purified by column chromatography or crystallized from a suitable solvent.

III. Taxane Starting Material

As noted above, the processes of the present invention may be utilized to convert taxanes of Formula (I) into protected taxane intermediates, which can then be used to further synthesize paclitaxel and docetaxel. Representative taxanes of Formular (I) include 10-deacetylbaccatin III (3) and baccatin III (4). However, other taxanes may also be present in the starting material without affecting the conversion of Formula (I) to Formula (III), as illustrated in Reaction Scheme 1. For example, taxanes present in a crude taxane extract or in a waste taxane solution may be present, in addition to a taxane of Formular (I). These taxanes are a plurality of compounds of a generic tetracyclic baccatin molecular framework as represented by Formula (IV):

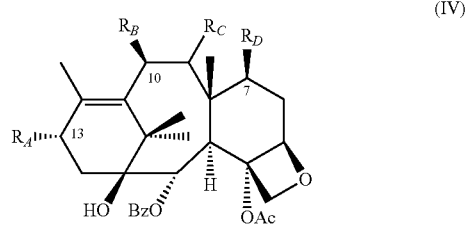

(IV)

wherein $R_A$, $R_B$, $R_C$ and $R_D$ represent substituents which vary between the taxanes. More specifically, $R_A$ is —OH, $R_B$ is —OH or —OAc, $R_C$ is =O, and $R_D$ is —OH or xylosyl. Representative taxanes can be present in the disclosed processes include 9-dihydro-13-acetylbaccatin III, paclitaxel, cephalomannine, 10-deacetyl taxol, 7-xylosyl taxol and 10-deacetyl-7-xylosyl taxol. It will be apparent to one skilled in the art that Formula (I) is a subset of the generic formula (IV), for example, when $R_A$ is —OH, $R_B$ is —OH, $R_c$ is =O and $R_D$ is —OH, the foregoing structure represents 10 deacetylbaccatin III, and when $R_A$ is —OH, $R_B$ is —OAc, $R_c$ is =O and $R_D$ is —OH, the foregoing structure represents baccatin III.

In certain embodiments, the taxanes utilized in the processes of the present invention may be pure, purified or partially purified taxanes. Such purified and partially purified taxanes may be obtained by any of a number of different methods well known in the art. For example, 10 deacetylbaccatin III can be obtained by the methods described in Gunawardana et al., J. Nat. Prod. 55:1686 (1992); U.S. Pat. No. 5,530,020 to Gunawardana et al.; U.S. Pat. Nos. 5,202, 448 and 5,256,801 to Carver et al., U.S. Pat. No. 5,449,790 to Zheng et al. and U.S. Pat. No. 6,281,368 to McChesney et al. which references are incorporated herein by reference in their entireties.

In other embodiments, the mixture of taxane utilized in the processes of the present invention may be a plurality of taxanes present in a crude taxane extract or in a waste taxane solution. In this way, the disclosed processes may be utilized for high yield and large scale conversion of taxanes present in a waste taxane solution into beta-lactam protected taxane intermediates, which can be used to further synthesize paclitaxel and docetaxel. Such waste taxane solutions may comprise (1) pooled waste stream fractions collected following the chromatographic separation and collection of paclitaxel enriched fractions from a crude or partially purified taxane extract, and/or (2) pooled waste mother liquors collected following the recrystallization of a crude or partially purified taxane extract.

Representative waste taxane solutions may be obtained by a number of different methods, such as, for example, the methods disclosed in U.S. Pat. No. 6,136,989 to Foo et al., and other references cited therein, which patent is incorporated herein by reference in its entirety, and U.S. patent application Ser. No. 10/831,648, which application is assigned to the assignee of the present invention and is incorporated herein by reference in its entirety. A representative method of obtaining a waste taxane solution, which comprises pooled waste stream fractions, comprises the following extraction and column chromatography steps.

Starting Taxane-Containing Material

A suitable taxane-containing material is any tissue that contains a high taxane content. Examples of suitable taxane-containing material include tissues from various species of Yew plants comprising the genus *Taxus*, most preferably the roots and needles of ornamental Yew plants such as *T. canadensis*, *T.×media spp Hicksii*, *T.×dark green spreader* and Hill., *T. chinensis*, *T. wallichiana*, *T. cuspidata*, *T. globosa*, *T. sumatrana*, *T. marei* and *T. floridana*, and the bark of *T. brevifolia* or *T. yunnanensis*. Other suitable material include cultures of plant tissues obtained from a *Taxus* species.

In a typical practice, such as set forth in U.S. Pat. No. 6,139,989, the taxane-containing material is either pulverized, chipped or otherwise ground into small pieces so as to increase efficiency of a solvent extraction. The taxane-containing material may also optionally be dried. Taxane-containing cell culture, cells, microorganisms and fermentation broths will typically be concentrated prior to solvent extraction. Cells and microorganisms can be processed as whole cells or cell paste or pulver.

Extraction

The taxane-containing material may be initially extracted by contacting the material with an organic solvent, usually for a prolonged period of at least 8 hours and typically for about 3 days with or without physical agitation to promote formation of a crude organic extract containing a plurality of taxanes. The extraction may employ any of the solvent systems that are known to be used for the extraction of paclitaxel, including but not limited to, acetone, methanol, ethanol, ethyl acetate, methylene chloride, chloroform, mixtures thereof, and mixtures containing an aqueous component of up to 60%. These solvents are typically added in an amount of about 4-20 liter per kg of the taxane-containing material to prepare the crude organic extract. Reference is made for example, to U.S. Pat. No. 6,136,989 and the publications cited therein which provide a non-exclusive description of several solvent systems that may be used to prepare an organic extract containing a plurality of taxanes.

In one embodiment, the organic solvent is a polar organic solvent, typically an alcohol. For some embodiments, methanol is preferred because of its low cost, ease of removal and efficiency of taxane extraction. In one embodiment, about 6-15 liters of methanol is added for every kg of taxane-containing material to be extracted. The extraction is accelerated by agitating the taxane-containing material, for example, by stirring or percolating the methanol with the taxane-containing material for about 1-5 days at a temperature between room temperature and about 60° C., most typically at about 40° C. When the taxane-containing material contains a paclitaxel content of at least 0.005%, methanol extraction for three days as described above recovers at least 90% of the available paclitaxel from the taxane-containing material, in addition to a plurality of other taxanes, to form a crude methanol extract containing about 0.1-0.5% paclitaxel and having an overall solid content of about 0.5-5% (w/v).

The large volume of methanol extract thus obtained is optionally concentrated, typically about 10-30 fold by evaporation to obtain a methanol extract concentrate having a solid content of about 100-400 g/L.

Liquid-Liquid Extraction

The crude organic extract may be subsequently enriched for taxanes by performing 1-3 liquid-liquid extractions by mixing the organic extract with a non-miscible, organic solvent to form a two phase system wherein one phase contains the plurality of taxanes. Generally, the two phase system includes a polar phase. Optionally, the taxane-containing phase is selected and concentrated by evaporation to form a concentrated extract having a solid content of about 100-400 g/L and a paclitaxel purity of about 1-4%. In some embodiments, water is included to help remove preferentially water soluble materials and the less polar solvent is selected to remove undesirable compounds such as waxes, lipids, pigments, and sterols that are found in different amounts depending on the taxane-containing material used. Typical solvents for liquid-liquid partitioning include hexane and methylene chloride. Methylene chloride has generally been found to be suitable for liquid-liquid extraction of taxane-containing material especially when the solvent used for the crude organic extract is an alcohol.

The concentrated extract obtained is optionally evaporated and the residue is re-dissolved in a solvent for loading onto a silica chromatography matrix.

Other example methods of performing a liquid-liquid extraction are illustrated in U.S. Pat. Nos. 5,475,120, 5,380,916, and 5,670,673 to Rao and references cited therein, and also in U.S. Pat. Nos. 5,618,538 and 5,480,639 to ElSohly et al. and references cited therein. These methods or variants thereof may alternatively be used in lieu of the embodiments described. Furthermore, liquid-liquid extraction may be omitted altogether when a plant extract containing high taxane levels is obtained by other methods such as for example, by intervening precipitation, crystallization or chromatography steps. One example of such a method is found in PCT Publication Nos. WO 98/07712 by Zamir et al, which uses a precipitation step immediately after obtaining an initial organic extract to obtain a paclitaxel fraction that may be about 1% or higher.

Silica Gel Column Chromatography

As further set forth in U.S. Pat. No. 6,136,989, the concentrated extract may be further purified by normal phase silica chromatography. As used herein, silica chromatography generally refers to the process of contacting a sample dissolved in a feed solvent with a silica matrix then eluting the silica matrix with an eluting solvent to obtain a fraction enriched with a desired component.

The dimensions of the first silica column are selected according to the quantity and purity of the solids to be separated. In one embodiment of a pilot scale process, about 250 grams of solids are dissolved in about 0.75 liters of feed solvent which is then chromatographed over a Silica column of about 1.5-inches×10-feet. In another embodiment, about 40-50 kg of solids are dissolved in about 100-200 liters of feed solvent, and chromatographed over a Silica column of about 18-inches×10-feet.

It has also been shown that a layer of about 1-15 cm of Celite, preferably about 2-8 cm, on top of the silica column is recommended as a column prefilter which substantially decreases the loading time of the sample. It has further been shown that the optimal eluting solvent for the Silica column should be a hexane/acetone mixture at a ratio of about 3:1 or a DCM/ethyl acetate mixture at a ratio of about 7:3. The "heart cut" fractions containing at least 2% paclitaxel are pooled and further purified, for example, according to the process set forth in U.S. Pat. No. 6,136,989. The remaining waste stream fractions, which contain a plurality of taxanes, including, paclitaxel, 10-deacetylbaccatin III (10-DAB), baccatin III (BACC III), 9-dihydro-13-acetylbaccatin III (9-DHB), cephalomannine, 10-deacetyl taxol (10-DAT), 7-xylosyl taxol and 10-deacetyl-7-xylosyl taxol are pooled into a waste taxane solution for further processing according to the present invention.

Further Purification Steps

As set forth in more detail in U.S. Pat. No. 6,139,989, the paclitaxel enriched "heart cut" fractions obtained from the foregoing chromatography step may be further purified through one or more additional chromatographic or recrystallization steps. Any waste stream fractions or waste mother liquors collected during such additional purification steps may also be pooled and added to the waste taxane solution for further processing according to the present invention.

IV. Side Chains and Precursors to the Side Chains

As noted above, the precursors to the side chains utilized in the semi-synthetic processes of the present invention can be beta-lactams, oxazolidines or oxazolines. As illustrated by the following examples and the attached figures, such precursors may be reacted with a taxane having a free hydroxyl group at the C-13 position according to processes of the present invention in order to attach a side chain to the C-13 position of the taxane.

Representative beta-lactams are compounds of Formula (II):

Figure 2:
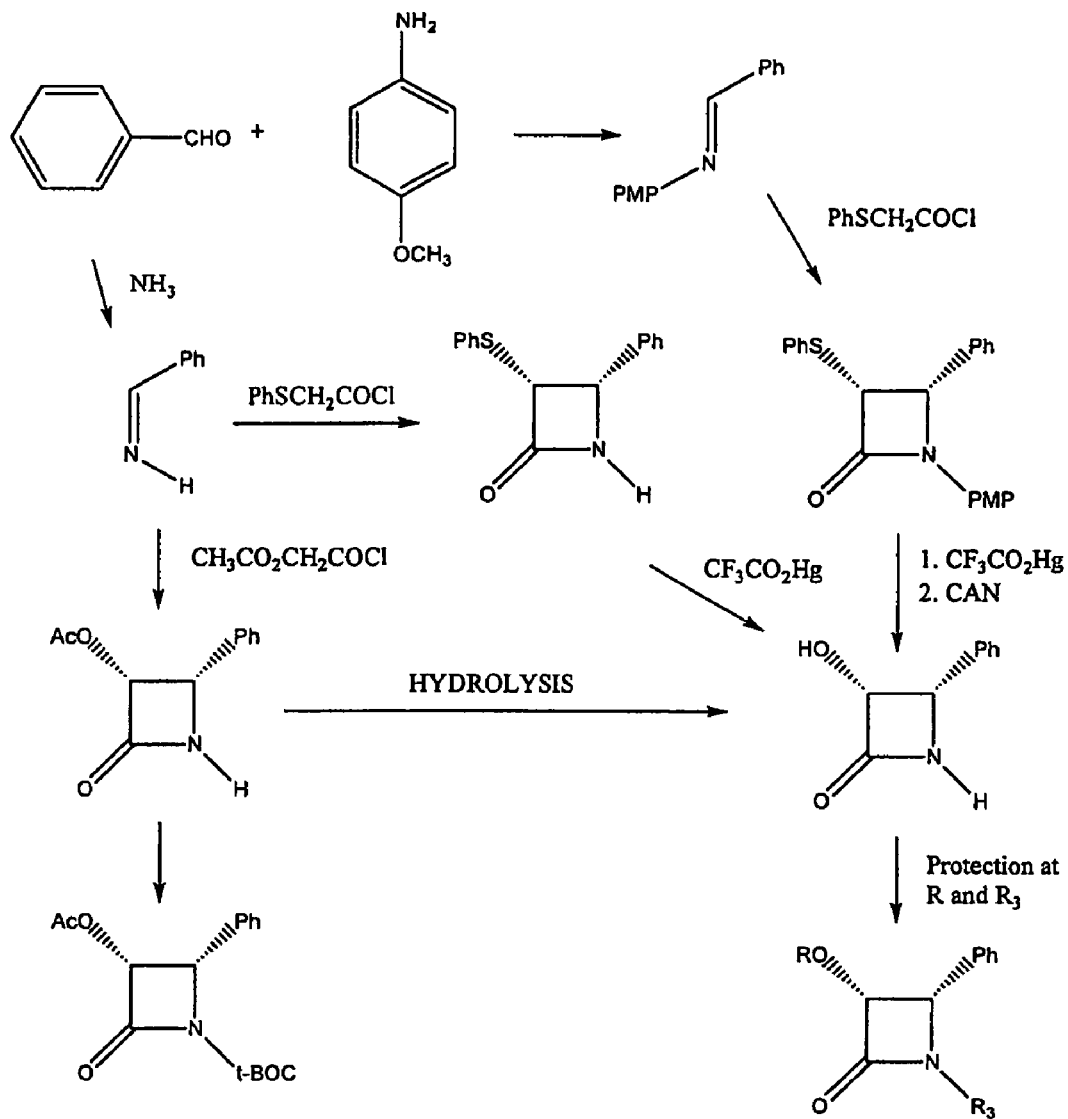
FIG. 2 illustrates several chemical routes for the preparation of beta-lactam side chains for use in the semi-synthetic processes of the present invention.

Formula (II)

wherein, $R_1$ is a hydroxy group, protected hydroxy group, thiol group or protected thiol group;

$R_2$ is alkyl, alkenyl, alkynyl or aryl; and $R_3$ is hydrogen, $C_1$-$C_6$ alkyl, aryl or acyl;

As described in U.S. patent application Ser. Nos. 10/683,865 and 10/790,622, which applications are assigned to the assignee of the present invention and are incorporated herein by reference in their entireties, and as shown in FIG. 2, such beta-lactams may be prepared according to Reaction

REACTION SCHEME 2

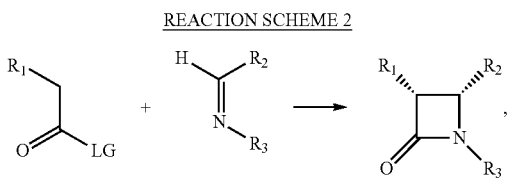

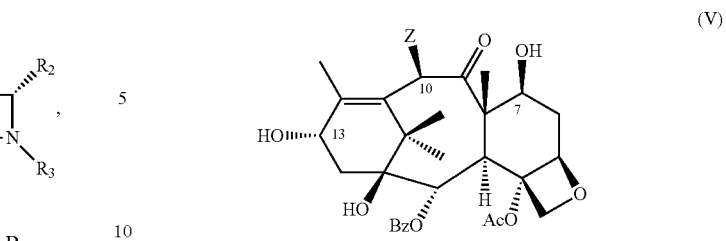

wherein LG is a leaving group and $R_1$, $R_2$ and $R_3$ are as defined above. In addition, as further described in the '865 patent, and as shown in FIG. 2, such beta-lactams may be further converted to other beta-lactam side chains.

U.S. patent application Ser. No. 10/790,622 (the "'622 patent") discloses beta-lactams having the structure:

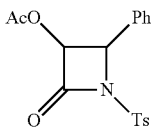

Figure 3:
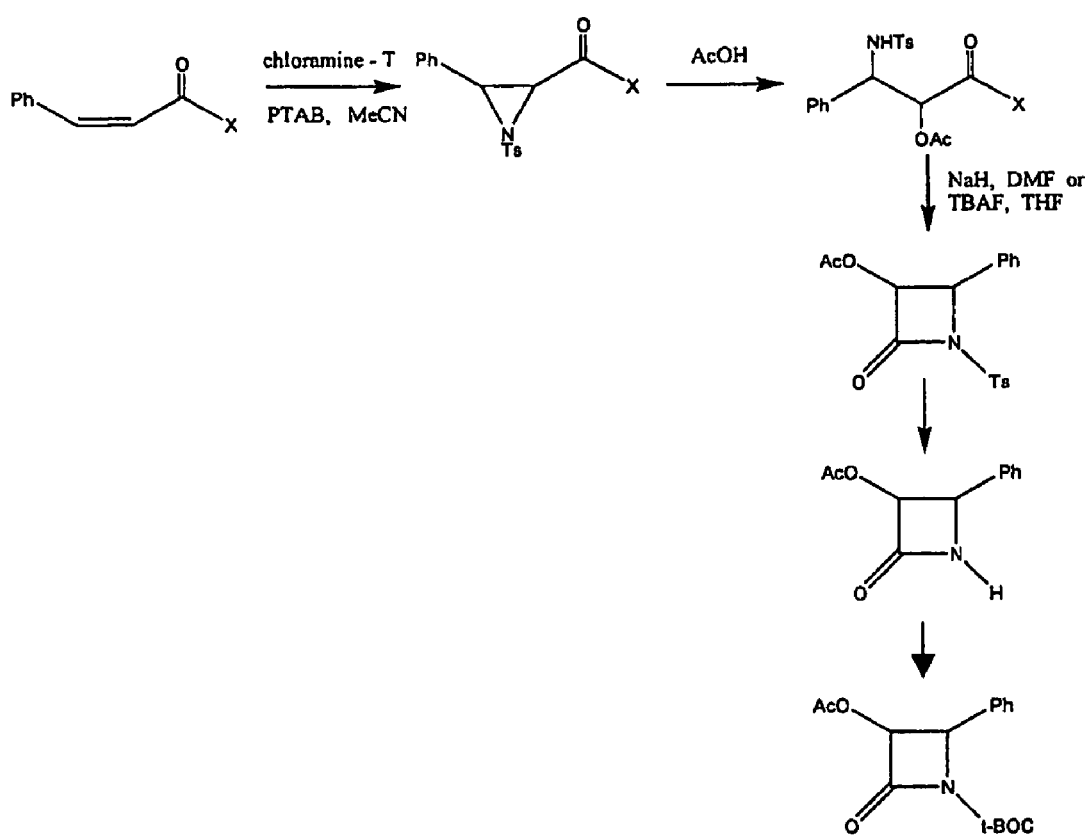
FIG. 3 illustrates an alternative chemical route for the preparation of a beta-lactam side chain for use in the semi-synthetic processes of the present invention.

As described in the '622 patent, and as shown in FIG. 3, such beta-lactams may be prepared by (1) converting cinnamoyl halide to a cinnamoyl halide aziridine intermediate having the structure:

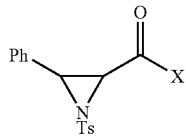

wherein X is halogen, (2) reacting the cinnamoyl halide aziridine intermediate with acetic acid to give an open chain cinnamoyl halide intermediate having the structure:

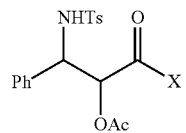

wherein X is halogen, and (3) converting the open chain cinnamoyl halide intermediate to the beta-lactams.

Representative oxazolidines and oxazolines are described in U.S. Pat. Nos. 6,365,750 and 6,307,071, and the references cited therein, which patents and references are incorporated herein by reference in their entireties.

V. Process of Preparing Paclitaxel or Docetaxel

As noted above, the C-13 protected taxane intermediates prepared according to the foregoing semi-synthetic processes may be utilized to further synthesize paclitaxel and docetaxel. In this regard, in one embodiment, the present invention provides an overall process for preparing paclitaxel and/or docetaxel, comprising:

(1) protecting the hydroxy group at the C-7 and/or C-10 position of a compound of Formula (V):

wherein, Z is —OH or protected —OH, (2) attaching a side chain to the free hydroxyl group at C-13 position to provide a C-13 protected taxane intermediate; and (3) converting the C-13 protected taxane intermediate to paclitaxel or docetaxel, wherein the steps of protecting and attaching comprise combining the compound of Formula (V) with a base, a suitable hydroxy protecting agent and a precursor to the side chain in a one pot reaction, and wherein the precursor to the side chain is beta-lactams, oxazolidines or oxazolines.

While Z can be any suitable hydroxy protecting group as described herein, in one embodiment, Z is —OAc, the compound of Formula (V) is therefore baccatin III. When Z is a free —OH, the compound of Formula (V) is 10 deacetylbaccatin III.

Suitable base for the protecting and attaching steps are as described above.

In a further embodiment, the present invention provides an overall process for preparing paclitaxel and/or docetaxel from an initial mixture of taxanes, wherein the initial mixture comprises 10-deacetylbaccatin III and at least one additional taxane selected from paclitaxel, baccatin III, cephalomannine, 9-dihydro-13-acetylbaccatin III, 10-deacetyl taxol, 7-xylosyl taxol and 10-deacetyl-7-xylosyl taxol, the process comprising:

(1) protecting the hydroxy group at the C-7 position of each taxane in the initial mixture having a hydroxy group at the C-7 position to provide a first intermediate mixture of C-7 protected taxanes;

(2) attaching a side chain to the C-13 position of each taxane having a free hydroxy group at the C-13 position in the first intermediate mixture to provide a mixture of C-13 protected taxane intermediates; and (3) converting the C-13 protected taxane intermediates to paclitaxel or docetaxel, wherein the step of protecting the C-7 and/or C-10 hydroxy groups and attaching a side chain to the free hydroxy at the C-13 position comprises, combining in one pot, the initial mixture with a base, a suitable hydroxy protecting agent and a precursor to the side chain, and wherein the precursor to the side chain is beta-lactams, oxazolidines or oxazolines.

In a further embodiment of the foregoing process, the step of protecting the hydroxy group at the C-7 position of each taxane in the initial mixture further comprises protecting a hydroxy group at the C-10 position of each taxane in the initial mixture having a hydroxy group at the C-10 position.

In other further embodiments, the initial mixture comprises: (1) 10-deacetylbaccatin III and at least two additional taxanes selected from paclitaxel, 9-dihydro-13-acetylbaccatin III, baccatin III, cephalomannine, 10-deacetyl taxol, 7-xylosyl taxol and 10-deacetyl-7-xylosyl taxol; (2) 10-deacetylbaccatin III and at least three additional taxanes selected from paclitaxel, 9-dihydro-13-acetylbaccatin III, baccatin III, cephalomannine, 10-deacetyl taxol, 7-xylosyl taxol and 10-deacetyl-7-xylosyl taxol; or (3) 10-deacetylbaccatin III, 9-dihydro-13-acetylbaccatin III, paclitaxel, baccatin III, cephalomannine, 10-deacetyl taxol, 7-xylosyl taxol and 10-deacetyl-7-xylosyl taxol.

In other further embodiments, the initial mixture of taxanes is a waste taxane solution comprising one or more of the following: (1) pooled waste stream fractions collected during a chromatographic separation of a crude or partially purified taxane extract; and (2) pooled waste mother liquors collected during a recrystallization of a crude or partially purified taxane extract. In two specific embodiments, the waste taxane solution comprises: (1) pooled waste stream fractions collected during a chromatographic separation of a crude taxane extract; and (2) pooled waste stream fractions collected during chromatographic separations of both crude and partially purified taxane extracts and pooled waste mother liquors collected during recrystallizations of both crude and partially purified taxane extracts.

In yet another embodiment, it is preferred that the first solvent is tetrahydrofuran. It is preferred to cool the first solution to a temperature of at least −40° C. Where the starting compound is either 10 deacetylbaccatin III or baccatin III, it is preferred to add at least two equivalents of the base.

In a further embodiment, the method described above can be expanded by adding the step of warming the second solution to at least 0° C. over a selected period of time, such as one hour. Further, the second solution may then be quenched with an agent effective to eliminate any excess of base and any excess of protecting agent in the solution to form a third solution. The method then includes concentrating the third solution to form a crude residue and purifying. The purification methodology may be accompanied by column chromatography or crystallization.

The resulting C-13 protected taxane intermediates may be converted to paclitaxel and docetaxel by a number of different methods, such as, for example, the methods disclosed in U.S. patent application Ser. Nos. 10/683,865 and 10/790,622, which applications are assigned to the assignee of the present invention and are incorporated herein by reference in their entireties, and U.S. Pat. Nos. 6,365,750 and 6,307,071, and the references cited therein, which patents and references are incorporated herein by reference in their entireties.

EXAMPLES

The following Examples disclose a representative process for synthesizing a C-13 beta-lactam protected taxane intermediate from 10 deacetylbaccatin III, and the subsequent conversion of such intermediate to docetaxel. Unless otherwise noted, all scientific and technical terms have the meanings as understood by one of ordinary skill in the art.

Example 1

Protection of C-7,10 Hydroxy Groups and Attachment of a Beta-Lactam Side Chain in a One Pot Reaction As shown in FIG. 1, to a stirred solution of 10-deacetylbaccatin III (10-DAB), in an organic solvent, such as THF, at around room temperature under an argon atmosphere was treated with a hydroxy-protecting agent, such as $Boc_2O$, in the presence of a base, such as 4-(N,N-dimethylamino)pyridine or n-BuLi or a mixture of n-BuLi/Li-t-OBu. The reaction was stirred at this temperature for a period between 30 minutes to 2 hours until complete consumption of the starting materials, as evidenced by TLC.

To this first solution of the C-7,10 protected 10-deacetylbaccatin III derivative in an organic solvent, such as the freshly distilled THF, under argon atmosphere at low temperature most preferably at −40 to −50° C., was added drop wise a solution of a base, such as n-BuLi, in hexanes or a mixture of n-BuLi/Li-t-OBu. After stirring for 30 min to 1 hr at this temperature, a solution of a beta-lactam in anhydrous THF was added drop wise to the mixture. The solution was slowly warmed to 0° C. and kept at that temperature for an additional 1 to 3 hrs, or until complete consumption of the starting material, as evidenced by TLC, before addition of a solution of an acid in an organic solvent, such as 10% AcOH in THF. The mixture was then partitioned between saturated aqueous sodium hydrogen carbonate and mixtures of dichloromethane and ethyl acetate. Evaporation of the organic layer yielded a crude C-13 beta-lactam protected taxane intermediate, which could be further purified by either column chromatography or crystallization to yield a pure C-13 beta-lactam protected taxane intermediate.

Example 2

Synthesis of Docetaxel

As further shown in FIG. 1, the C-13 beta-lactam protected taxane intermediate, was hydrolyzed using formic acid to remove the C-7 and/or C-10 BOC protecting group and then with a mixture of $NaHCO_3/Na_2CO_3/H_2O_2$ to deprotect the C-2' and/or C-10 acetate groups to yield docetaxel, as described in U.S. application Ser. No. 10/790,622, which application is assigned to the assignee of the present invention and is incorporated herein by reference in its entirety.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:
1. A method of making C-13 protected taxane intermediate in a one-pot synthesis, comprising:
   protecting the free hydroxy groups at the C-7 position and/or the C-10 position of the taxane of Formula (I):

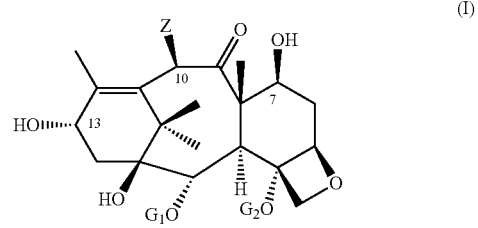

wherein, Z is —OH or a protected —OH, and $G_1$ and $G_2$ are the same or different hydroxy protecting group;
   reacting the protected compound of Formula (I) with a beta-lactam, oxazolidine or oxazolines to form a C-13 protected taxane intermediate,
   wherein the reaction is conducted in the presence of a base.

2. The process of claim 1 wherein the precursor to the side chain is a beta-lactam of formula (II):

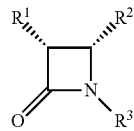

Formula (II)

wherein,
$R_1$ is a hydroxy group, protected hydroxy group, thiol group or protected thiol group;
$R_2$ is alkyl, alkenyl, alkynyl or aryl; and
$R_3$ is hydrogen, $C_1$-$C_6$ alkyl, aryl or acyl.

3. The process of claim 2 wherein the beta-lactam has the structure:

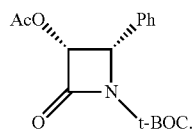

4. The process of claim 1 wherein Z is —OH or —OAc.
5. The process of claim 1 wherein $G_1$ is benzoyl and $G_2$ is acetyl.
6. The process of claim 5 wherein the compound of Formula (I) is 10-deacetylbaccatin III or baccatin III.
7. The process of claim 1 wherein the base is DMAP, pyridine, TEA, LiOH, Li-t-OBu, n-BuLi, LiH, LiHMDS, KHMDS, K-t-OBu, NaH, NaHMDS or a mixture of any two or more of the foregoing.
8. The process of claim 1 wherein the combined steps of protecting and attaching in a one pot reaction further comprises combining the taxane of Formula (I) with a metal alkoxide, wherein the metal is selected from the group consisting of Group I, II and III metals and transition metals.
9. The process of claim 8 wherein the metal is lithium, sodium or potassium.
10. The process of claim 1 wherein the hydroxy protecting agent is an alkylating agent, a silylating agent or an acylating agent.
11. The process of claim 10 wherein the hydroxy-protecting group is tert-butoxycarbonyl (t-BOC), benzyloxycarbonyl (CBZ), 2,2,2-trichloroethoxycarbonyl (Troc), 9-fluorenyl methoxycarbonyl (Fmoc), 2,2,2-trichloroethoxymethyl, trimethyl silyl, triethyl silyl, dimethyl(t-butyl) silyl, diethylmethylsilyl, dimethyl phenylsilyl, diphenylmethylsilyl, acetyl, chloroacetyl, dichloroacetyl trichloroacetyl or trifluoroacetyl.
12. The process of claim 11 wherein the base is DMAP or n-BuLi and the hydroxy-protecting agent is tert-butoxycarbonyl or dichloroacetyl.
13. The process of claim 1 wherein the taxane of Formula (I) is part of a mixture of taxanes comprising a taxane of Formula (I), paclitaxel, 9-dihydro-13-acetylbaccatin III, cephalomannine, 10-deacetyl taxol, 7-xylosyl taxol and 10-deacetyl-7-xylosyl taxol.
14. A method of making a C-13 protected taxane intermediate in a one-pot synthesis, for converting to paclitaxel or docetaxel, comprising:
(1) protecting with a suitable protecting group, the hydroxy group at the C-7 and/or C-10 position of a compound of formula (V):

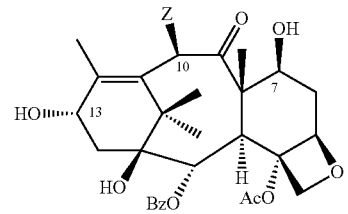

(V)

wherein, Z is —OH or protected —OH,
(2) reacting the protected compound of Formula (V) with a beta-lactam, oxazolidine or oxazolines, in the presence of a base, to provide a C-13 protected taxane intermediate; and
(3) converting the C-13 protected taxane intermediate to paclitaxel or docetaxel.

15. The process of claim 14 wherein the compound of Formula (V) is 10-deacetylbaccatin III or baccatin III.
16. The process of claim 14 wherein the precursor to the side chain is a beta-lactam of formula (II):

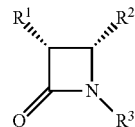

Formula (II)

wherein,
$R_1$ is a hydroxy group, protected hydroxy group, thiol group or protected thiol group;
$R_2$ is alkyl, alkenyl, alkynyl or aryl; and
$R_3$ is hydrogen, $C_1$-$C_6$ alkyl, aryl or acyl.

17. The process of claim 16 wherein the beta-lactam has the structure:

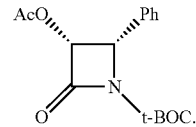

18. The process of claim 14 wherein the base is DMAP, pyridine, TEA, LiOH, Li-t-OBu, n-BuLi, LiH, LiHMDS, KHMDS, K-t-OBu, NaH, NaHMDS or a mixture of any two or more of the foregoing.
19. The process of claim 14 wherein the hydroxy protecting agent is an alkylating agent, a silylating agent or an acylating agent.
20. The process of claim 19 wherein the hydroxy-protecting group is tert-butoxycarbonyl (t-BOC), benzyloxycarbonyl (CBZ), 2,2,2-trichloroethoxycarbonyl (Troc), 9-fluorenyl methoxycarbonyl (Fmoc), 2,2,2-trichloroethoxymethyl, trimethyl silyl, triethyl silyl, dimethyl(t-butyl)silyl, diethylmethylsilyl, dimethyl phenylsilyl, diphenylmethylsilyl, acetyl, chloroacetyl, dichloroacetyl trichloroacetyl or trifluoroacetyl.
21. A method for preparing paclitaxel or docetaxel from an initial mixture of taxanes comprising 10-deacetylbaccatin III and at least one additional taxane selected from paclitaxel, 9-dihydro-13-acetylbaccatin III, baccatin III, cephalomannine, 10-deacetyl taxol, 7-xylosyl taxol and 10-deacetyl-7-xylosyl taxol, comprising:

(1) protecting the hydroxy group at the C-7 position of each taxane in the initial mixture having a hydroxy group at the C-7 position to yield a first intermediate mixture of C-7 protected taxanes;
(2) attaching a side chain to the C-13 position of each taxane having a free hydroxy group at the C-13 position in the first intermediate mixture to provide a mixture of C-13 protected taxane intermediates; and
(3) converting the C-13 protected taxane intermediates to paclitaxel or docetaxel,
wherein the steps of protecting the C-7 hydroxy groups and attaching a side chain to the free hydroxyl at the C-13 position comprises: combining, in a one pot reaction, the initial mixture with a base, a suitable hydroxy protecting agent and a precursor to the side chain, and wherein the precursor to the side chain is a beta-lactam, oxazolidine or oxazoline.

22. The process of claim 21 wherein the precursor to the side chain is a beta-lactam of

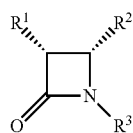

Formula (II)

wherein,
$R_1$ is a hydroxy group, protected hydroxy group, thiol group or protected thiol group;
$R_2$ is alkyl, alkenyl, alkynyl or aryl; and
$R_3$ is hydrogen, $C_1$-$C_6$ alkyl, aryl or acyl.

23. The process of claim 22 wherein the beta-lactam has the structure:

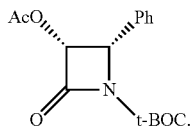

24. The process of claim 21 wherein the step of protecting the hydroxy group at the C-7 position of each taxane in the initial mixture further comprises protecting a free hydroxy group at the C-10 position of each taxane in the initial mixture having a hydroxy group at the C-10 position.

25. The process of claim 21 wherein the initial mixture comprises 10-deacetylbaccatin III and at least two additional taxanes selected from paclitaxel, 9-dihydro-13-acetylbaccatin III, baccatin III, cephalomannine, 10-deacetyl taxol, 7-xylosyl taxol and 10-deacetyl-7-xylosyl taxol.

26. The process of claim 21 wherein the initial mixture comprises 10-deacetylbaccatin III and at least three additional taxanes selected from paclitaxel, 9-dihydro-13-acetylbaccatin III, baccatin III, cephalomannine, 10-deacetyl taxol, 7-xylosyl taxol and 10-deacetyl-7-xylosyl taxol.

27. The process of claim 21 wherein the initial mixture comprises 10-deacetylbaccatin III, paclitaxel, 9-dihydro-13-acetylbaccatin III, baccatin III, cephalomannine, 10-deacetyl taxol, 7-xylosyl taxol and 10-deacetyl-7-xylosyl taxol.

28. The process of claim 21 wherein the initial mixture of taxanes is a waste taxane solution comprising one or more of the following:
pooled waste stream fractions collected during a chromatographic separation of a crude or partially purified taxane extract; and
pooled waste mother liquors collected during a recrystallization of a crude or partially purified taxane extract.

29. The process of claim 28 wherein the waste taxane solution comprises pooled waste stream fractions collected during a chromatographic separation of a crude taxane extract.

30. The process of claim 28 wherein the waste taxane solution comprises pooled waste stream fractions collected during chromatographic separations of both crude and partially purified taxane extracts and pooled waste mother liquors collected during recrystallizations of both crude and partially purified taxane extracts.

31. The process of claim 28 wherein the crude and partially purified taxane extracts are obtained from taxane-containing materials from the genus *Taxus*.

32. The process of claim 21 wherein the base is DMAP, pyridine, TEA, LiOH, Li-t-OBu, n-BuLi, LiH, LiHMDS, KHMDS, K-t-OBu, NaH, NaHMDS or a mixture of any two or more of the foregoing.

33. The process of claim 21 wherein the hydroxy protecting agent is an alkylating agent, a silylating agent or an acylating agent.

34. The process of claim 33 wherein the hydroxy-protecting group is tert-butoxycarbonyl (t-BOC), benzyloxycarbonyl (CBZ), 2,2,2-trichloroethoxycarbonyl (Troc), 9-fluorenyl methoxycarbonyl (Fmoc), 2,2,2-trichloroethoxymethyl, trimethyl silyl, triethyl silyl, dimethyl(t-butyl)silyl, diethylmethylsilyl, dimethyl phenylsilyl, diphenylmethylsilyl, acetyl, chloroacetyl, dichloroacetyl trichloroacetyl or trifluoroacetyl.

* * * * *